(12) United States Patent
Lecuivre

(10) Patent No.: US 11,359,313 B2
(45) Date of Patent: *Jun. 14, 2022

(54) PROSTHETIC POROUS KNIT

(71) Applicant: SOFRADIM PRODUCTION, Trevoux (FR)

(72) Inventor: Julie Lecuivre, Jassans-Riottier (FR)

(73) Assignee: SOFRADIM PRODUCTION, Trevoux (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/995,763

(22) Filed: Aug. 17, 2020

(65) Prior Publication Data

US 2020/0378043 A1   Dec. 3, 2020

Related U.S. Application Data

(63) Continuation of application No. 15/920,577, filed on Mar. 14, 2018, now Pat. No. 10,745,835, which is a
(Continued)

(30) Foreign Application Priority Data

Dec. 5, 2014   (EP) ..................................... 14306956

(51) Int. Cl.
*D04B 21/12*   (2006.01)
*A61F 2/00*   (2006.01)
*D04B 1/22*   (2006.01)

(52) U.S. Cl.
CPC ............ *D04B 21/12* (2013.01); *A61F 2/0063* (2013.01); *D04B 1/22* (2013.01);
(Continued)

(58) Field of Classification Search
CPC ........ D04B 21/10; D04B 21/12; D04B 21/20; D04B 21/22; A61F 2/0063;
(Continued)

(56) References Cited

U.S. PATENT DOCUMENTS

| | | | |
|---|---|---|---|
| 1,187,158 | A | 6/1916 | Mcginley |
| 3,118,294 | A | 1/1964 | Van Laethem |

(Continued)

FOREIGN PATENT DOCUMENTS

| | | |
|---|---|---|
| CA | 1317836 C | 5/1993 |
| CN | 103533910 A | 1/2014 |

(Continued)

OTHER PUBLICATIONS

Examination Report No. 1 issued in Australian Patent Application No. 2020200947 dated Oct. 29, 2020, 3 pages.

(Continued)

*Primary Examiner* — Danny Worrell
(74) *Attorney, Agent, or Firm* — Weber Rosselli & Cannon LLP

(57) ABSTRACT

The invention relates to a prosthetic porous knit based on a monofilament of a biocompatible polymer material, the pattern followed for the knitting of said monofilament on a warp knitting machine having two guide bars B1, B2 being the following, according to the ISO 11676 standard:
  Bar B1: 1.2/4.5/4.3/4.5/4.3/1.0/1.2/1.0//
  Bar B2: 4.3/1.0/1.2/1.0/1.2/4.5/4.3/4.5//
The invention further relates to a method for producing such a knit and to a hernia prosthesis comprising such a knit.

17 Claims, 4 Drawing Sheets

Related U.S. Application Data continuation of application No. 14/928,082, filed on Oct. 30, 2015, now Pat. No. 9,932,695.

(52) U.S. Cl.
CPC . *A61F 2002/0068* (2013.01); *A61F 2240/001* (2013.01); *D10B 2509/08* (2013.01)

(58) Field of Classification Search
CPC ....... A61F 2002/0068; A61F 2240/001; D10B 2509/08
See application file for complete search history.

(56) References Cited

U.S. PATENT DOCUMENTS

| | | |
|---|---|---|
| 3,124,136 A | 3/1964 | Usher |
| 3,272,204 A | 9/1966 | Artandi et al. |
| 3,276,448 A | 10/1966 | Kronenthal |
| 3,320,649 A | 5/1967 | Naimer |
| 3,364,200 A | 1/1968 | Ashton et al. |
| 3,570,482 A | 3/1971 | Shigeru et al. |
| 4,006,747 A | 2/1977 | Kronenthal et al. |
| 4,060,081 A | 11/1977 | Yannas et al. |
| 4,173,131 A | 11/1979 | Melton et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,476,697 A | 10/1984 | Schafer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,841,962 A | 6/1989 | Berg et al. |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 5,002,551 A | 3/1991 | Linsky et al. |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,254,133 A | 10/1993 | Seid |
| 5,256,418 A | 10/1993 | Kemp et al. |
| 5,263,983 A | 11/1993 | Yoshizato et al. |
| 5,304,595 A | 4/1994 | Rhee et al. |
| 5,306,500 A | 4/1994 | Rhee et al. |
| 5,324,775 A | 6/1994 | Rhee et al. |
| 5,328,955 A | 7/1994 | Rhee et al. |
| 5,334,527 A | 8/1994 | Brysk |
| 5,339,657 A | 8/1994 | Mcmurray |
| 5,350,583 A | 9/1994 | Yoshizato et al. |
| 5,356,432 A | 10/1994 | Rutkow et al. |
| 5,368,549 A | 11/1994 | Mcvicker |
| 5,376,375 A | 12/1994 | Rhee et al. |
| 5,376,376 A | 12/1994 | Li |
| 5,397,331 A | 3/1995 | Himpens et al. |
| 5,399,361 A | 3/1995 | Song et al. |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,681,568 A | 10/1997 | Goldin et al. |
| 5,686,115 A | 11/1997 | Vournakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,709,934 A | 1/1998 | Bell et al. |
| 5,716,409 A | 2/1998 | Debbas |
| 5,720,981 A | 2/1998 | Eisinger |
| 5,732,572 A | 3/1998 | Litton |
| 5,749,895 A | 5/1998 | Sawyer et al. |
| 5,752,974 A | 5/1998 | Rhee et al. |
| 5,766,246 A | 6/1998 | Mulhauser et al. |
| 5,766,631 A | 6/1998 | Arnold |
| 5,769,864 A | 6/1998 | Kugel |
| 5,771,716 A | 6/1998 | Schlussel |
| 5,785,983 A | 7/1998 | Furlan et al. |
| 5,800,541 A | 9/1998 | Rhee et al. |
| 5,814,328 A | 9/1998 | Gunasekaran |
| 5,833,705 A | 11/1998 | Ken et al. |
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | Mcgregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,906,937 A | 5/1999 | Sugiyama et al. |
| 5,910,149 A | 6/1999 | Kuzmak |
| 5,911,731 A | 6/1999 | Pham et al. |
| 5,916,225 A | 6/1999 | Kugel |
| 5,919,232 A | 7/1999 | Chaffringeon et al. |
| 5,919,233 A | 7/1999 | Knopf et al. |
| 5,922,026 A | 7/1999 | Chin |
| 5,931,165 A | 8/1999 | Reich et al. |
| 5,942,278 A | 8/1999 | Hagedorn et al. |
| 5,962,136 A | 10/1999 | Dewez et al. |
| 5,972,022 A | 10/1999 | Huxel |

(56) References Cited

U.S. PATENT DOCUMENTS

| | | |
|---|---|---|
| RE36,370 E | 11/1999 | Li |
| 5,993,844 A | 11/1999 | Abraham et al. |
| 5,994,325 A | 11/1999 | Roufa et al. |
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |
| 6,039,686 A | 3/2000 | Robert |
| 6,042,534 A | 3/2000 | Gellman et al. |
| 6,042,592 A | 3/2000 | Schmitt |
| 6,043,089 A | 3/2000 | Sugiyama et al. |
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,120,539 A | 9/2000 | Eldridge et al. |
| 6,132,765 A | 10/2000 | Dicosmo et al. |
| 6,143,037 A | 11/2000 | Goldstein et al. |
| 6,153,292 A | 11/2000 | Bell et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,197,325 B1 | 3/2001 | Macphee et al. |
| 6,197,934 B1 | 3/2001 | Devore et al. |
| 6,197,935 B1 | 3/2001 | Doillon et al. |
| 6,210,439 B1 | 4/2001 | Firmin et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,424 B1 | 10/2001 | Vyakarnam et al. |
| 6,312,474 B1 | 11/2001 | Francis et al. |
| 6,328,686 B1 | 12/2001 | Robert |
| 6,334,872 B1 | 1/2002 | Termin et al. |
| 6,383,201 B1 | 5/2002 | Dong |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | Devore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,500,464 B2 | 12/2002 | Ceres et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,613,348 B1 | 9/2003 | Jain |
| 6,623,963 B1 | 9/2003 | Mueller et al. |
| 6,630,414 B1 | 10/2003 | Matsumoto |
| 6,638,284 B1 | 10/2003 | Rousseau et al. |
| 6,652,594 B2 | 11/2003 | Francis et al. |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,682,760 B2 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,719,795 B1 | 4/2004 | Bryan et al. |
| 6,723,335 B1 | 4/2004 | Moehlenbruck et al. |
| 6,730,299 B1 | 5/2004 | Tayot et al. |
| 6,743,435 B2 | 6/2004 | Devore et al. |
| 6,755,868 B2 | 6/2004 | Rousseau |
| 6,773,723 B1 | 8/2004 | Spiro et al. |
| 6,790,213 B2 | 9/2004 | Cherok et al. |
| 6,790,454 B1 | 9/2004 | Abdul et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,893,653 B2 | 5/2005 | Abraham et al. |
| 6,896,904 B2 | 5/2005 | Spiro et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,988,386 B1 | 1/2006 | Okawa et al. |
| 7,025,063 B2 | 4/2006 | Snitkin et al. |
| 7,041,868 B2 | 5/2006 | Greene et al. |
| RE39,172 E | 7/2006 | Bayon et al. |
| 7,098,315 B2 | 8/2006 | Schaufler |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,594,921 B2 | 9/2009 | Browning |
| 7,614,258 B2 | 11/2009 | Cherok et al. |
| 7,670,380 B2 | 3/2010 | Cauthen, III et al. |
| 8,418,508 B2 | 4/2013 | Lecuivre et al. |
| 9,308,070 B2 | 4/2016 | Mortarino et al. |
| 9,932,695 B2 | 4/2018 | Lecuivre et al. |
| 2001/0008930 A1 | 7/2001 | Tayot et al. |
| 2002/0095218 A1 | 7/2002 | Carr et al. |
| 2002/0116070 A1 | 8/2002 | Amara et al. |
| 2003/0013989 A1 | 1/2003 | Obermiller et al. |
| 2003/0023316 A1 | 1/2003 | Brown et al. |
| 2003/0086975 A1 | 5/2003 | Ringeisen |
| 2003/0100954 A1 | 5/2003 | Schuldt-Hempe et al. |
| 2003/0114937 A1 | 6/2003 | Leatherbury et al. |
| 2003/0133967 A1 | 7/2003 | Ruszczak et al. |
| 2003/0212460 A1 | 11/2003 | Darois et al. |
| 2003/0225355 A1 | 12/2003 | Butler |
| 2003/0232746 A1 | 12/2003 | Lamberti et al. |
| 2004/0034373 A1 | 2/2004 | Schuldt-Hempe et al. |
| 2004/0054406 A1 | 3/2004 | Dubson et al. |
| 2004/0059356 A1 | 3/2004 | Gingras |

(56) References Cited

U.S. PATENT DOCUMENTS

| | | | |
|---|---|---|---|
| 2004/0101546 A1 | 5/2004 | Gorman et al. |
| 2004/0138762 A1 | 7/2004 | Therin et al. |
| 2004/0172048 A1 | 9/2004 | Browning |
| 2004/0215219 A1 | 10/2004 | Eldridge et al. |
| 2005/0002893 A1 | 1/2005 | Goldmann |
| 2005/0010306 A1 | 1/2005 | Priewe et al. |
| 2005/0021058 A1 | 1/2005 | Negro |
| 2005/0085924 A1 | 4/2005 | Darois et al. |
| 2005/0113849 A1 | 5/2005 | Popadiuk et al. |
| 2005/0113938 A1 | 5/2005 | Jamiolkowski et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0228408 A1 | 10/2005 | Fricke et al. |
| 2005/0232979 A1 | 10/2005 | Shoshan |
| 2005/0244455 A1 | 11/2005 | Greenawalt |
| 2005/0267521 A1 | 12/2005 | Forsberg |
| 2005/0288691 A1 | 12/2005 | Leiboff |
| 2006/0094318 A1 | 5/2006 | Matsuda et al. |
| 2006/0135921 A1 | 6/2006 | Wiercinski et al. |
| 2006/0147501 A1 | 7/2006 | Hillas et al. |
| 2006/0167561 A1 | 7/2006 | Odar et al. |
| 2006/0216320 A1 | 9/2006 | Kitazono et al. |
| 2006/0252981 A1 | 11/2006 | Matsuda et al. |
| 2007/0031474 A1 | 2/2007 | Tayot et al. |
| 2007/0161109 A1 | 7/2007 | Archibald et al. |
| 2007/0280990 A1 | 12/2007 | Stopek |
| 2007/0297987 A1 | 12/2007 | Stad et al. |
| 2007/0299538 A1 | 12/2007 | Roeber |
| 2008/0147198 A1 | 6/2008 | Cherok et al. |
| 2010/0016872 A1 | 1/2010 | Bayon et al. |
| 2010/0191088 A1 | 7/2010 | Anderson et al. |
| 2011/0295565 A1 | 12/2011 | Ozen |
| 2012/0198894 A1 | 8/2012 | Lecuivre et al. |

FOREIGN PATENT DOCUMENTS

| | | |
|---|---|---|
| CN | 103534397 A | 1/2014 |
| CN | 105147416 A | 12/2015 |
| DE | 19544162 C1 | 4/1997 |
| DE | 10019604 A1 | 10/2001 |
| DE | 10043396 C1 | 6/2002 |
| EP | 0194192 A1 | 9/1986 |
| EP | 0248544 A1 | 12/1987 |
| EP | 0276890 A2 | 8/1988 |
| EP | 0372969 A1 | 6/1990 |
| EP | 0544485 A1 | 6/1993 |
| EP | 0552576 A1 | 7/1993 |
| EP | 0614650 A2 | 9/1994 |
| EP | 0621014 A1 | 10/1994 |
| EP | 0625891 A1 | 11/1994 |
| EP | 0637452 A1 | 2/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 0827724 A2 | 3/1998 |
| EP | 0836838 A1 | 4/1998 |
| EP | 0895762 A2 | 2/1999 |
| EP | 0898944 A2 | 3/1999 |
| EP | 1017415 A1 | 7/2000 |
| EP | 1052319 A1 | 11/2000 |
| EP | 1055757 A1 | 11/2000 |
| EP | 1216215 A1 | 6/2002 |
| EP | 1216718 A1 | 6/2002 |
| EP | 0693523 B1 | 11/2002 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1782848 A2 | 5/2007 |
| FR | 2244853 A1 | 4/1975 |
| FR | 2257262 A1 | 8/1975 |
| FR | 2308349 A1 | 11/1976 |
| FR | 2453231 A1 | 10/1980 |
| FR | 2715405 A1 | 7/1995 |
| FR | 2724563 A1 | 3/1996 |
| FR | 2744906 A1 | 8/1997 |
| FR | 2766698 A1 | 2/1999 |
| FR | 2771622 A1 | 6/1999 |
| FR | 2779937 A1 | 12/1999 |
| FR | 2859624 B1 | 12/2005 |
| FR | 2863277 B1 | 6/2006 |
| FR | 2884706 B1 | 4/2008 |
| GB | 2051153 A | 1/1981 |
| JP | H0332677 U | 3/1991 |
| JP | H05237128 A | 9/1993 |
| JP | H09137380 A | 5/1997 |
| JP | 2002518129 A | 6/2002 |
| JP | 2011505220 A | 2/2011 |
| WO | 8902445 A1 | 3/1989 |
| WO | 8908467 A1 | 9/1989 |
| WO | 9012551 A1 | 11/1990 |
| WO | 9206639 A2 | 4/1992 |
| WO | 9207648 A2 | 5/1992 |
| WO | 9220349 A1 | 11/1992 |
| WO | 9302168 A1 | 2/1993 |
| WO | 9311805 A1 | 6/1993 |
| WO | 9318174 A1 | 9/1993 |
| WO | 9417747 A1 | 8/1994 |
| WO | 9507666 A1 | 3/1995 |
| WO | 9518638 A1 | 7/1995 |
| WO | 9532687 A1 | 12/1995 |
| WO | 9603091 A1 | 2/1996 |
| WO | 9608277 A1 | 3/1996 |
| WO | 9609795 A1 | 4/1996 |
| WO | 9614805 A1 | 5/1996 |
| WO | 9641588 A1 | 12/1996 |
| WO | 9702789 A1 | 1/1997 |
| WO | 9735533 A1 | 10/1997 |
| WO | 9835632 A1 | 8/1998 |
| WO | 9849967 A1 | 11/1998 |
| WO | 9905990 A1 | 2/1999 |
| WO | 9906079 A1 | 2/1999 |
| WO | 9906080 A1 | 2/1999 |
| WO | 9951163 A1 | 10/1999 |
| WO | 0016821 A1 | 3/2000 |
| WO | 0067663 A1 | 11/2000 |
| WO | 0115625 A1 | 3/2001 |
| WO | 0180773 A1 | 11/2001 |
| WO | 02078568 A1 | 10/2002 |
| WO | 2004004600 A1 | 1/2004 |
| WO | 2004071349 A2 | 8/2004 |
| WO | 2004078120 A2 | 9/2004 |
| WO | 2004103212 A1 | 12/2004 |
| WO | 2005011280 A1 | 2/2005 |
| WO | 2005013863 A2 | 2/2005 |
| WO | 2005018698 A1 | 3/2005 |
| WO | 2005105172 A1 | 11/2005 |
| WO | 2006018552 A1 | 2/2006 |
| WO | 2006023444 A2 | 3/2006 |
| WO | 2007048099 A3 | 9/2010 |
| WO | 2011042811 A2 | 4/2011 |
| WO | 2012123582 A1 | 9/2012 |

OTHER PUBLICATIONS

Notification of Second Office Action issued in Chinese Application No. 201910285263.4 dated May 6, 2021, with English translation.
Amid, P., "Lichtenstein tension-free hernioplasty: Its inception, evolution, and principles," Hernia, 2004; pp. 1-7, 8, published online Sep. 2003.
Blondin, C. et al., "Inhibition of Complement Activation by Natural Sulfated Polysaccharides (Fucans) from Brown Seaweed," Molecular Immuol., Mar. 1994, pp. 247-253, 31(4).
Blondin, C. et al., "Relationships between chemical characteristics and anticomplementary activity of fucans," Biomaterials, Mar. 1996, pp. 597-603, 17(6).
Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).

(56) References Cited

OTHER PUBLICATIONS

Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.
Collins, R. et al., "Use of collagen film as a dural substitute: Preliminary animal studies," Journal of Biomedical Materials Research, Feb. 1991, pp. 267-276, vol. 25.
Ellouali, M. et al., "Antitumor Activity of Low Molecular Weight Fucans Extracted from Brown Seaweed Ascophyllum Nodosum," Anticancer Res., Nov.-Dec. 1993,pp. 2011-2020, 12 (6A).
European Search Report for EP 14306956.5 date of completion is May 20, 2015 (4 pages).
Examination Report No. 1 issued is Australian Patent Application No. 2015249131 dated Jul. 5, 2019, 4 pages.
Haneji, K et al., "Fucoidan extracted from Cladosiphon Okamuranus Tokida Induces Apoptosis of Human T-cell Leukemia Virus Type 1—Infected T-Cell Lines and Primary Adult T-Cell Leukemia Cells," Nutrition and Cancer, 2005, pp. 189-201, 52(2),published online Nov. 2009.
Haroun-Bouhedja, F. et al., “In Vitro Effects of Fucans on MDA-MB231 Tumor Cell Adhesion and Invasion, Anticancer Res., Jul.-Aug. 2002, pp. 2285-2292, 22(4).
Haroun-Bouhedja, F. et al., "Relationship between sulfate groups and biological activities of fucans," Thrombosis Res., Dec. 2000, pp. 453-459, 100(5).
Hirano, S. et al., "The blood biocompatibility of chitosan and N-acylchitosans," J. Biomed. Mater. Res., Apr. 1985, 413-417, 19.
Japanese Office Action issued in JP Patent Application No. 2015-230410 dated Jul. 26, 2019 with English translation, 5 pages.
Junge, K. et al., "Functional and Morphologic Properties of a Modified Mesh for Inguinal Hernia Repair," World J. Surg., Sep. 2002, pp. 1472-1480, 26.
Kanabar, V. et al., "Some structural determinants of the antiproliferative effect of heparin-like molecules on human airway smooth muscle," Br. J. Pharmacol., Oct. 2005, pp. 370-777, 146(3).
Klinge, U. et al., "Foreign Body Reaction to Meshes Used for the Repair of Abdominal Wall Hernias," Eur J. Surg, Sep. 1999, pp. 665-673, 165.
Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.
Langenbech, M. R. et al., "Comparison of biomaterials in the early postoperative period," Surg Enclose., May 2003, pp. 1105-1109, 17 (7).
Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).
Malette, W. G. et al., "Chitosan, A New Hemostatic," Ann Th. Surg., Jul. 1983, pp. 55-58, 36.
Muzzarelli, R. et al., "Reconstruction of parodontal tissue with chitosan," Biomaterials, Nov. 1989, pp. 598-604, 10.
Notice of Allowance issued in Japanese patent application No. 2015-230410 dated Dec. 3, 2019; with English translation; 5 pages.
Notification of the First Office Action issued in Chinese Application No. 201710183803.9 dated Aug. 28, 2020, 34 pages.
Notification of the First Office Action issued in Chinese Patent Application No. 201910285263.4 dated Sep. 1, 2020, 14 pages.
O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).
Preliminary Search Report from French Patent Office dated Dec. 20, 2006, 3 pages.
Prokop, A. et al., "Water Soluble Polymers for Immunoisolation I: Complex Coacevation and Cytotoxicity," Advances in Polymer Science, Jul. 1998, pp. 1-51, 136.
Rao, B. et al., "Use of chitosan as a biomaterial: Studies on its safety and hemostatic potential," J. Biomed. Mater. Res., Jan. 1997, pp. 21-28, 34.
Rosen, M. et al., "Laparoscopic component separation in the single-stage treatment of infected abdominal wall prosthetic removal," Hernia, 2007, pp. 435-440, 11, published online Jul. 2007.
Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004,pp. 211-220, 18(2).
Strand, S. et al., "Screening of Chitosans and Conditions for Bacterial Flocculation," Biomacromolecules, Mar. 2001, 126-133, 2.
T Muhl. et al., "New Objective Measurement to Characterize the Porosity of Textile Implants," Wiley Interscience, Journal of Biomedical Materials ResearchPart B: Applied Biomaterials, May 11, 2007, p. 176-183.
Varum, K. et al., "In vitro degradation rates of partially N-acetylated chitosans in human serum," Carbohydrate Research, Mar. 1997, pp. 99-101, 299.
Welty, G. et al., "Functional impairment and complaints following incisional hernia repair with different polypropylene meshes," Hernia, Aug. 2001; pp. 142-147, 5.
Zvyagintseva, T. et al., "Inhibition of complement activation by water-soluble polysaccharides of some far-eastern brown seaweeds," Comparative Biochem and Physiol, Jul. 2000, pp. 209-215, 126(3).
Canadian Office Action issued in Canadian Patent application No. 2,911,337 dated Oct. 12, 2021.

PROSTHETIC POROUS KNIT

CROSS-REFERENCE TO RELATED APPLICATIONS

This application is a continuation of U.S. patent application Ser. No. 15/920,577 filed Mar. 14, 2018, which is a continuation application of U.S. patent application Ser. No. 14/928,082 filed Oct. 30, 2015, now U.S. Pat. No. 9,932,695, which claims benefit of and priority to European Patent Application No. 14306956 filed Dec. 5, 2014, the disclosures of each of the above-identified applications are hereby incorporated by reference in their entirety.

TECHNICAL FIELD

The present invention relates to a prosthetic porous knit useful in parietal surgery, the knit having a lightweight and macroporous structure while showing good mechanical strength properties.

BACKGROUND

Wall-reinforcing prostheses, for example prostheses for reinforcing the abdominal wall, are widely used in the surgical field. These prostheses are intended to treat hernias by temporarily or permanently filling a tissue defect. These prostheses are generally made of biocompatible prosthetic fabric, in particular prosthetic knits, and can have a number of shapes, for example rectangular, circular or oval, depending on the anatomical structure to which they are to be fitted.

In a view of reducing the foreign material implanted into the body of a patient, it is desired to produce lightweight knits, intended to be used as wall reinforcing prostheses. In addition, for facilitating the work of the surgeon at the time he puts the prosthesis in place at the implantation site, it is further desired that the prosthetic knit show a good transparency. Moreover, the wall reinforcing prosthesis should also favor a good tissue ingrowth. In this view, it is desired that the knit used for wall reinforcing prostheses show a plurality of pores, and preferably large pores.

Lightweight porous knits usable in the manufacture of wall reinforcing prostheses already exist. Nevertheless, they sometimes show poor mechanical strength. Indeed, the knit is generally pliant and soft in order to conform to the abdominal wall and flex with movement of the abdominal wall once implanted. The knit may be held in place by suturing, stapling, or tacking the knit to surrounding biological tissue. In particular, existing lightweight porous knits may show a poor resistance to fracture when they are sutured or tacked to the surrounding biological tissue.

In addition, the performance of the abdominal wall hernia repair using a prosthetic knit fixed on the abdominal wall depends in part upon the shear forces experienced at the knit fixation points. These shear forces may be quite high as a result of high intra-abdominal pressure.

Too high shear forces at knit fixation points, once the knit or prosthesis is implanted and has been fixed for example by sutures at the abdominal wall, may lead to abdominal wall repair recurrences and/or generate pain for the patient. The distribution of shear forces at fixation points is important to assess the safety and the efficacy of the abdominal wall repair.

SUMMARY

In particular, it would be desirable to provide a prosthesis made from a knit for which the distribution of the shear forces at fixation points is as regular as possible and for which the value of shear forces at fixation points is as low as possible, so that the prosthesis may for example be introduced at the implantation site and implanted without the surgeon having to check for a specific position of the warp or weft direction of the knit. It would further be desirable to provide a prosthesis made from a knit for which the risk of fixation pull out and/or implant failure at fixation points is reduced.

In addition, if a knit is too pliant and soft, it may not resist sufficiently to the intra abdominal pressure during specific movements of the patient, for example when the patient coughs or jumps. The knit may then be prone to undesired bulging phenomenon and may not ensure sufficient reinforcement of the abdominal wall in such conditions.

There is therefore a need for a porous prosthetic knit that would be capable of having a lightweight and macroporous structure while at the same time show good mechanical strength properties.

A first aspect of the invention is a prosthetic porous knit based on a monofilament of a biocompatible polymer material, the pattern followed for the knitting of said monofilament on a knitting machine having two guide bars B1, B2 being the following, according to the ISO 11676 standard:

Bar B1: 1.2/4.5/4.3/4.5/4.3/1.0/1.2/1.0//
Bar B2: 4.3/1.0/1.2/1.0/1.2/4.5/4.3/4.5//

Another aspect of the invention is a method for manufacturing the prosthetic knit above comprising the step of producing a knit with a monofilament of a biocompatible polymer material on a knitting machine having two guide bars B1, B2 according to the following pattern, according to the ISO 11676 standard:

Bar B1: 1.2/4.5/4.3/4.5/4.3/1.0/1.2/1.0//
Bar B2: 4.3/1.0/1.2/1.0/1.2/4.5/4.3/4.5//

Guide bars B1 and B2 may be threaded 1 full 1 empty and may move symmetrically.

The knitting machine may be a warp knitting machine or a raschel knitting machine.

The knit of the invention is porous. In particular, the knit of the invention comprises openings or pores: these openings or pores are in particular generated by the pattern followed for the knitting of the monofilament of the knit according to the invention. The porosity of the knit of the invention confers to the knit a transparency allowing the surgeon to have a good visibility of the implantation site at the time he puts the knit or prosthesis in place.

The knit of the invention is lightweight. The knit of the invention preferably shows a mass per unit area ranging from about 40 to about 70 $g/m^2$, preferably ranging from about 40 to about 50 $g/m^2$, and more preferably of about 44 $g/m^2$, 45 $g/m^2$, 46 $g/m^2$, 47 $g/m^2$ or 48 $g/m^2$, measured according to ISO 3801: 1977 «Determination of mass per unit length and mass per unit area», 5 specimens 1 $dm^2$. Such a low mass per unit area allows introducing only a little quantity of foreign material in the body of the patient.

The knit of the invention is made from a monofilament of biocompatible polymer material.

The biocompatible polymer may be synthetic or natural. The biocompatible polymer may be biodegradable, non-biodegradable or a combination of biodegradable and non-biodegradable. The term "biodegradable" as used herein is defined to include both bioabsorbable and bioresorbable materials. By biodegradable, it is meant that the materials decompose, or lose structural integrity under body conditions (e.g., enzymatic degradation or hydrolysis) or are broken down (physically or chemically) under physiologic conditions in the body such that the degradation products are excretable or absorbable by the body.

The biocompatible polymer may be selected from the group consisting of biodegradable polymers, non-biodegradable polymers, and combinations thereof.

In embodiments, the biocompatible polymer material is selected from polypropylene, polyester such as polyethylene terephthalates, polyamide, silicone, polyether ether ketone (PEEK), polyarylether ether ketone (PAEK) polylactic acid (PLA), polycaprolactone (PCL), polydioxanone (PDO), trimethylene carbonate (TMC), polyvinyl alcohol (PVA), polyhydroxyalkanoate (PHA), polyglycolic acid (PGA), copolymers of these materials, and mixtures thereof.

In embodiments, the biocompatible polymer material is polypropylene.

In embodiments, the monofilament has a diameter of from about 0.08 mm to about 0.25 mm, preferably from about 0.10 mm to 0.15 mm, more preferably of about 0.11 mm, 0.12 mm, or 0.13 mm. Such a diameter allows obtaining a good size of the pores and maintaining the lightweight structure of the knit, while maintaining good mechanical properties. In embodiments, the monofilament has a diameter of about 0.12 mm.

In embodiments, the knit comprises a plurality of pores having a diameter above 1 mm. In particular, the plurality of pores having a diameter above 1 mm defines an efficient porosity of said knit ranging from about 35% to about 70%, preferably of about 55%.

By "efficient porosity" is meant according to the present application a porosity taking into account only the pores having a diameter above 1 mm, while leaving out the pores having a diameter less or equal to 1 mm. By "pores having a diameter above 1 mm" is meant the pores which have dimensions greater than 1 mm in all directions. The efficient porosity therefore corresponds to the ratio of the area of the totality of the pores having a diameter above 1 mm as defined above to the area of the totality of the knit studied. The pores having a diameter above 1 mm are measured with a profile projector such as a projector 300V from ORAMA. The "efficient porosity" and its measuring method are described in the publication "*New objective measurements to characterize the porosity of textile implants*", T. Mühl, M. Binnebösel, U. Klinge and T. Goedderz, Journal of Biomedical Materials Research Part B: Applied Biomaterials, p. 176-183.

The efficient porosity as described above is useful for characterizing the ability of the knit to favor cell colonization. Indeed, pores having a diameter above 1 mm are particularly desired for tissue ingrowth after implantation.

The knitting pattern of the knit of the invention defines a plurality of pores having a diameter ranging above 1 mm. The pores may have a substantially hexagonal or circular shape.

In embodiments, the knit of the invention comprises a plurality of pores having a diameter above 2 mm. Such knits with pores having a diameter above 2 mm favor cell colonization and exhibit a good transparency allowing the surgeon to have a better visibility of the surrounding tissues when he puts the knit/prosthesis in place at the implantation site.

In embodiments, the knit of the invention has a tensile breaking strength in the warp direction of at least about 200 N, preferably of about 237 N. In embodiments, the knit of the invention has a tensile breaking strength in the weft direction of at least about 170 N, preferably of about 201 N. In embodiments, the knit of the invention has a bursting strength of at least about 400 kPa, preferably of about 463 kPa. In embodiments, the knit of the invention has a tear strength in the warp direction of at least about 25 N, preferably of about 30 N. In embodiments, the knit of the invention has a tear strength in the weft direction of at least about 25 N, preferably of about 37 N. In embodiments, the knit of the invention has a suture pull out strength in the warp direction of at least about 35 N, preferably of about 46 N. In embodiments, the knit of the invention has a suture pull out strength in the weft direction of at least about 38 N, preferably of about 42 N. In embodiments, the knit of the invention has a tensile strength of at least about 42 N/cm, preferably of about 47 N/cm.

The tensile breaking strength (N), the bursting strength (kPa), the tear strength (N), the suture pull out strength (N) and the tensile strength (N/cm) above are measured according to the methods as indicated in the below Example of the present application.

Following knitting and heat-setting, the knit can be cleaned, packaged and sterilized using conventionally known techniques. The knit of the invention can be used as provided in the package or cut to any desired dimension once removed from the package.

The knit of the invention can be implanted in extraperitoneal site either for inguinal or ventral hernia repair via open or laparoscopic approach. Fixation to the surrounding tissues can be achieved by stapling, conventional sutures or other means.

The prosthetic knit of the invention shows an homogeneous distribution of shear forces at fixation points. In particular, although it is provided with a lightweight structure, the prosthetic knit of the invention shows a good resistance to fracture at fixation points compared to lightweight knits of the prior art.

The knit of the invention may be used on its own as a prosthesis to be implanted into in a patient for hernia repair for example.

Another aspect of the invention is a hernia prosthesis comprising a knit as described above.

BRIEF DESCRIPTION OF THE DRAWINGS

The present invention will become clearer from the following description and from the attached drawings, in which.

DETAILED DESCRIPTION

Figure 1:
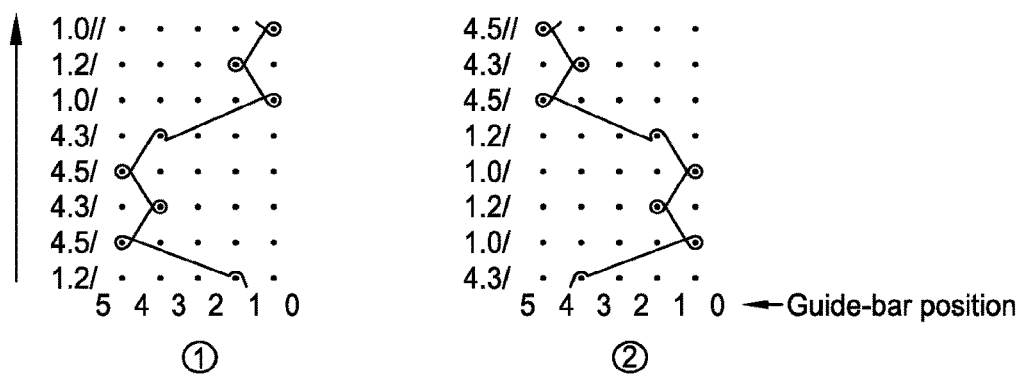
FIG. 1 is a schematic view of the knitting pattern of a knit of the invention.

With reference to FIG. 1, is shown a graphic representing the knitting pattern of the knit of the invention, namely the following pattern according to the ISO 11676 standard:

Bar B1: 1.2/4.5/4.3/4.5/4.3/1.0/1.2/1.0//
Bar B2: 4.3/1.0/1.2/1.0/1.2/4.5/4.3/4.5//

The overall pattern repetition size of the knit of the invention is eight courses. FIG. 1 depicts only one thread from guide bar B1 and one thread from guide bar B2 to better show the movement of the thread. The evolution of the threads at the ninth course is the same as at the first course.

Figure 2:
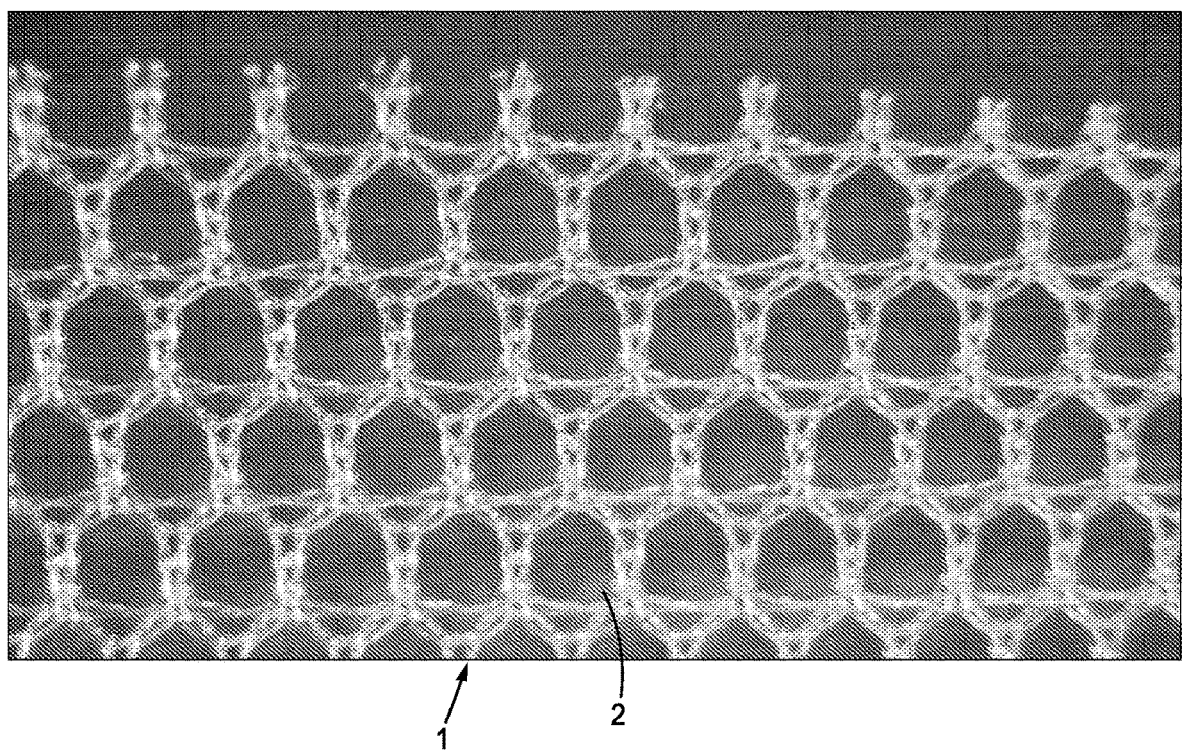
FIG. 2 is a front view of the knit of the invention obtained with the knitting pattern of FIG. 1.

With reference to FIG. 2, is shown a photograph of the knit 1 of the invention obtained with the knitting pattern as represented in FIG. 1.

The knit 1 of FIG. 2 was obtained from a monofilament of polypropylene of diameter 0.12 mm.

The knitting pattern of the knit of the invention produces pores greater than about 1.0 mm in diameter. For example, the principal pores 2 of the knit 1 of FIG. 2 have an average size of 2.0×2.4 mm. Such a large size of pores is very favorable for cell colonization and confers to the knit a good transparency allowing a good visibility at the implantation site.

The knit of the invention shows an homogeneous distribution of the shear forces at fixation points. The distribution of the shear forces at fixation points may be evaluated with a system for assessing shear forces distribution at fixation points of textile-based implants, such as an axisymmetrical experimental set-up as described in reference to FIGS. 3 and 4, such a system allowing exhibiting the capability of a textile to distribute shear forces at fixation points without integrating specific geometrical considerations.

Figure 3:
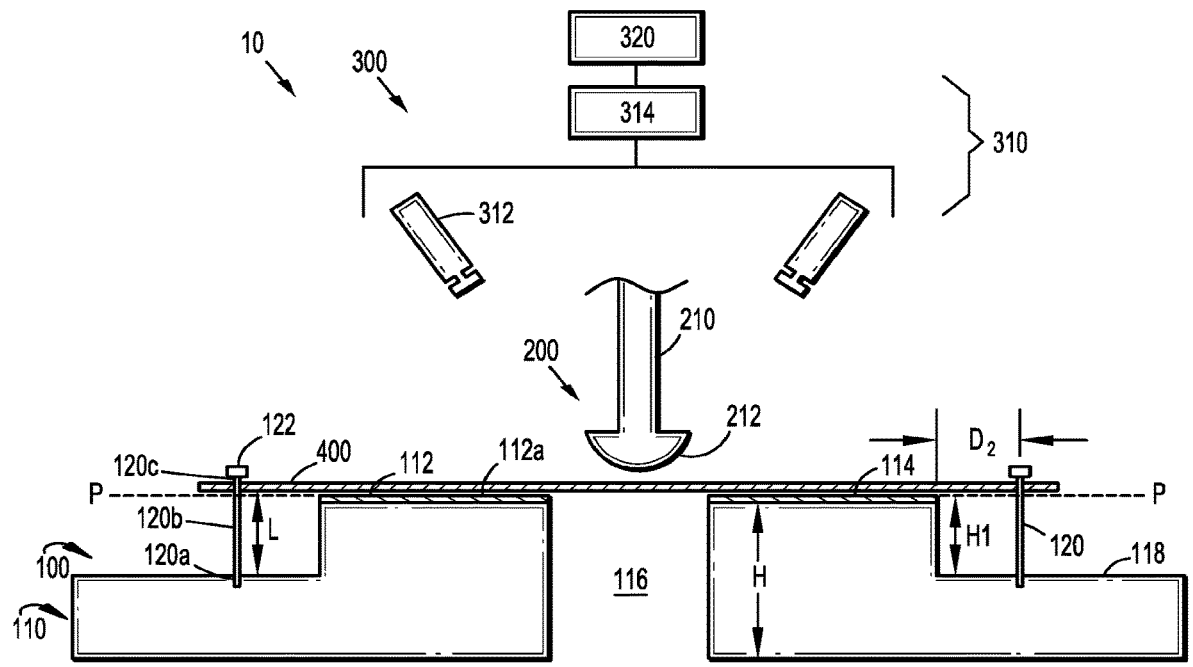
FIG. 3 is a side view of a schematic configuration of a system for measuring the distribution of the shear forces at fixation points of a knit.
Figure 4:
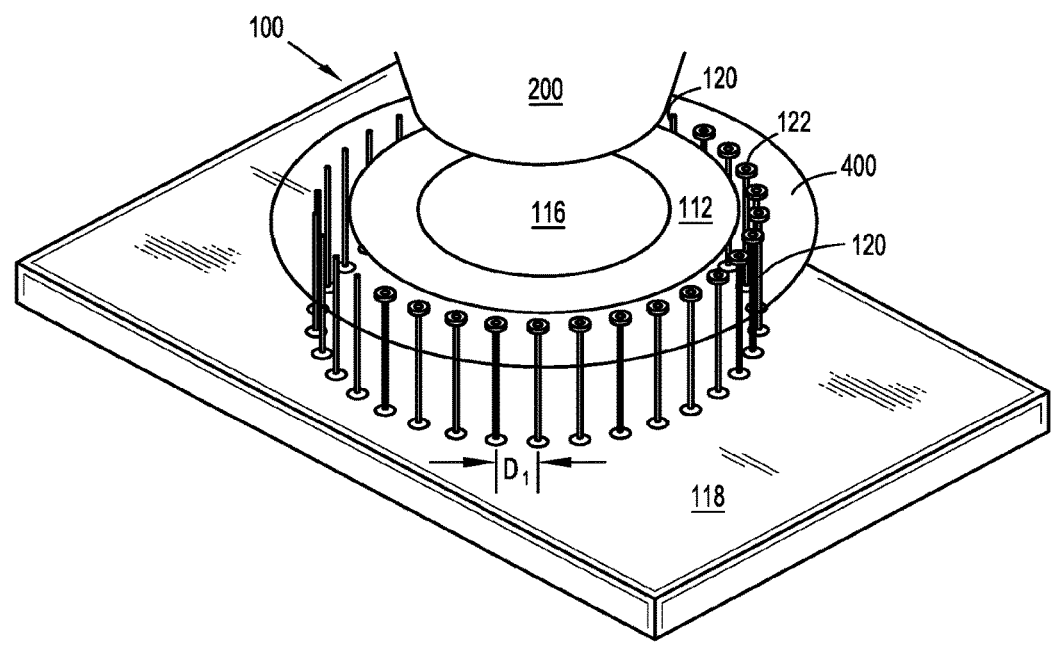
FIG. 4 is an enlarged perspective view of a portion of the system of FIG. 3.

Referring now to FIGS. 3 and 4, system 10 includes a tissue model 100, a load simulation device 200, and an analysis system 300 for assessing characteristics of a textile-based implant 400 when fixed to the tissue model 100 and subjected to a load exerted by the load simulation device 200. The tissue model 100 includes a base 110 having an upper surface 112 extending along a plane "P" and having a closed outer perimeter 114 that defines an opening 116 therethrough. The upper surface 112 is configured to mimic the inner surface of an abdominal wall: it is flat and horizontal. The opening 116 defined through the upper surface 112 is configured to mimic a defect in an abdominal wall and may be referred to herein as the "defect". The opening 116 has a circular shape and a uniform size and dimension through the height "H" of the base 110. In the system of FIG. 3, the opening 116 is an empty circle having a radius of 55 mm with a 10 mm fillet.

The upper surface 112 is covered by a coating 112a having a coefficient of friction that mimics the frictional coefficient of an inner surface abdominal wall against a textile-based implant 400. The coefficient of friction is about 0.3.

The base 110 includes a lower planar surface 118 that is stepped down from the upper planar surface 112 at a pre-determined height "H1" and extends around the upper surface 112.

The base 110 also includes a fixation support under the form of a plurality of rods 120, configured to secure a textile-based implant 400 thereto at two or more fixation points. The plurality of rods 120 are attached to the lower surface 118 at a predetermined distance "D1" of 20 mm from each other and a predetermined distance "D2" of 70 mm from the upper surface 112 extremity. The rods 120 are arranged in a simple circle crown fixation, centered to the opening 116. Each rod 120 includes a first end 120a fixed to the lower surface 118, an elongate body 120b extending from the lower surface 118 towards the upper surface 112 and defining a length "L" of 60 mm, and a second end 120c terminating about or above the plane "P" defined by the upper surface 112. The elongate body 120b extends perpendicularly from the lower surface 118. The rods 120 are threaded rod M3, with an equivalent radius of 2.5 mm and a Young Modulus of 110 Gpa.

The rods 120 are configured for direct fixation to a portion of the textile-based implant 400 when the textile-based implant 400 is placed upon the upper surface 112 of the tissue model 100 over the opening 116 in the upper surface 112. The tension at the fixation points in the textile-based implant 400 is minimum. Markers 122 are attached to the second end 120c of the rods 120 such that the markers 122 are disposed about or above the plane "P" defined by the upper surface 112. Each marker 122 is under the form of a white circle of diameter 5 mm within a black circle of diameter of 10 mm and is localized 8 mm above the textile-based implant 400. Markers 122 provide a visual indication of the position of the rods 120. Markers 122 are distributed on half of the textile-based implant 400 from two warp extremities.

The load simulation device 200 is positioned above the upper surface 112 of the base 110 and is configured to simulate a change in environmental loading conditions surrounding the tissue model 100 such that changes in load are generated about the tissue model 100. The load may be referred to herein as the "intra abdominal pressure equivalent." As shown, the load simulation device 200 is a plunger 210 including a contacting surface 212 that is hemispherical (diameter 100 mm) and that is centered over the opening 116 defined through the upper surface 112. The plunger 210 is configured to move in a direction perpendicular to the plane "P" of the upper surface 112 and exert a predetermined force, referred to hereinafter as the plunger force, against the textile-based implant 400 so that the implant 400 engages the opening 116 defined within the upper surface 112 of the tissue model 100. The load simulation device 200 is capable of applying a quasi-static pressure (low plunger 210 descent velocity) on the textile-based implant 400 to simulate various physiological conditions. For example, the plunger force applied may be of 147 N, namely 116 mmHg, which corresponds to the intra abdominal pressure when the patient is in a standing valsalva condition. Alternatively, the plunger force applied may be of 304 N, namely 240 mmHg, which corresponds to the intra abdominal pressure when the patient jumps.

The analysis system 300 includes a digital image acquisition and processing component 310 including two cameras 312 for recording the position of the markers 122 in a 3D coordinate system and digital image correlation software 314, namely Vic 3D™ from the company Correlated Solutions for calculating the displacement vector of each of the markers 122 resulting from bending of the rods 120 in response to the loads exerted on the textile-based implant 400 by the load simulation device 200. The analysis system 300 records the plunger displacement 210. The analysis system 300 also includes a mathematical software component 320 that is utilized to calculate the shear force vector at each fixation point where a marker 122 exists using the displacement vector component in the plane "P" of the markers 122 and the continuum mechanics theory applied to the rods 120. Accordingly, each shear force vector is a function of the "intra abdominal pressure equivalent." The mathematical software component 320 may include any numerical software package, such as, for example, MATLAB® from the company Matchworks.

An indication on the bulging of the textile-based implant 400 through the opening 116 may be given by the assessment of the plunger penetration through the opening 116.

In an exemplary method of use, a textile-based implant 400, such as a prosthetic knit, is placed on the upper surface 112 of the base 110 of the tissue model 100 such that the implant 400 lies along the plane "P" defined by the upper surface 112. The implant 400 is centered placed about the opening 116 in the upper surface 112 and, as should be understood by a person of ordinary skill in the art, the orientation of the fibers of the implant 400 is controlled with respect to the upper surface 112. The textile-based implant 400 is then directly fixed to the plurality of fixation rods 120. A plurality of markers 122 are then affixed to a portion of the fixation rods 120 such that the markers 122 extend between the two warp extremities of the implant 400.

With the implant 400 fixed to the tissue model 100, the analysis system 300 is activated such that the cameras 312 capture the position of the markers 122 in a 3D coordinate system. The acquisition of the position/positional changes of the markers 122 via the cameras 312 is synchronized with the activation of the load simulation device 200 as the forces applied to the implant 400 by the load simulation device 200 is transferred to the rods 120 at the fixation points and results in bending of the rods 120. Accordingly, any movement of the rods 120 results in movement of the markers 122 which is recorded by the cameras 312 and used in determining the shear force vector at each fixation point as described above.

As will appear from the Example below, the system of FIGS. 3 and 4 allows evaluating the properties of prosthetic knits regarding the distribution of shear forces at fixation points, bulging phenomenon and fracture at fixation points.

The advantages of the knit of the invention will appear more clearly in the Example below.

EXAMPLE

Two lightweight knits of the prior art (Knits A and B) and a knit of the invention (knit C) have been produced as described below.

Knit A: knit A is a knit of the prior art as described in WO2011/042811, namely obtained by knitting a monofilament of polyethylene terephthalate of diameter 0.08 mm on a warp knitting machine having two guide bars B1, B2, according to the following pattern, according to the ISO 11676 standard:

Bar B1: 1.0/1.2/1.0/2.3/2.1/2.3/4.5/4.3/4.5/3.2/3.4/3.2//
Bar B2: 4.5/4.3/4.5/3.2/3.4/3.2/1.0/1.2/1.0/2.3/2.1/2.3//

Guide bars B1 and B2 are threaded 1 full 1 empty and move symmetrically.

Knit B: knit B is a knit of the prior art as described in U.S. Pat. No. 6,408,656, namely obtained by knitting a monofilament of polypropylene of diameter 0.10 mm on a warp knitting machine having two guide bars B1, B2, according to the following pattern, according to the ISO 11676 standard:

Bar B1: 5.4/4.3/2.1/0.1/1.2/3.4//
Bar B2: 0.1/1.2/3.4/5.4/4.3/2.1//

Guide bars B1 and B2 are threaded 1 full 1 empty and move symmetrically.

Knit C: is a knit of the invention obtained with the knitting pattern of FIG. 1, by knitting a monofilament of polypropylene of diameter 0.12 mm knitted on a warp knitting machine having two guide bars B1, B2, the pattern followed being the following, according to the ISO 11676 standard:

Bar B1: 1.2/4.5/4.3/4.5/4.3/1.0/1.2/1.0//
Bar B2: 4.3/1.0/1.2/1.0/1.2/4.5/4.3/4.5//

Guide bars B1 and B2 are threaded 1 full 1 empty and move symmetrically.

The following properties of knits A, B and C have been determined as follows:

Mass per unit area (g/m$^2$): measured according to ISO 3801: 1977 «Determination of mass per unit length and mass per unit area», 5 specimens 1 dm$^2$, pore size (width×height) (mm): knit biggest pores are measured making one measurement on 10 individual samples with a profile projector such as a projector 300V from ORAMA, Bursting strength (kPa): measured according to ISO 13938-2: 1999 "Textiles—Bursting properties of textiles—Pneumatic method for determining the bursting strength and bursting deformation", 5 samples Tensile strength (N/cm) is measured through a plunger test with a traction testing machine such as the Hounsfield model H5KS (Hounsfield, Redhill, England), crosshead speed: 50 mm/min, 5 samples: the burst pressure can be determined using a circular mesh sample with a radius of $R_m$=56.4 mm and with a test area of 100 cm$^2$ clamped at the outward boarder (modified DIN 54307 superseded standard). Then, the mesh is loaded with a spherical stamp of a radius $R_s$=50 mm, velocity v=50 mm/min until rupture occurs. Based on the measured forces and the resulting stretch, the tensile strength (N/cm) can be calculated;

Tear strength (N) in the warp direction and in the weft direction: measured according to ISO 4674:1977 "Textiles covered with rubber or plastic—Determination of the tear strength" Method A2, 5 samples, width: 75 mm, Tear length≤145 mm, crosshead speed: 100 mm/min, Thickness: is measured according to ISO 9073-2: 1997 "Textiles—test methods for nonwovens—Part 2: Determination of thickness", 10 samples, 100×50 mm, Tensile breaking strength and elongation at break: is measured according to ISO 13934-1: 2013 "Textiles—Tensile properties of fabrics—Part 1: Determination of maximum force and elongation at maximum force using the strip method", 5 samples, width: 50 mm, Length: 200 mm between the jaws, Crosshead speed: 100 mm/min, Pre-load: 0.5 N, using a traction testing machine such as the Hounsfield model H5KS (Hounsfield, Redhill, England);

Effective porosity: pores having a diameter above 1 mm are measured with a profile projector such as a projector 300V from ORAMA, 1 sample of 100×50 mm;

Suture pull out strength in the warp direction and in the weft direction measured according to NF S94-801: 2007 "Reinforcement implants introduced by the vaginal route for the treatment of stress urinary incontinence and/or of prolapse of the pelvic organs—pre-clinical trials and clinical trials"—§ 5.3.3 5 specimens 50×100 mm, USP 2 suture yarn, crosshead speed: 100 mm/min, using a traction testing machine such as the Hounsfield model H5KS (Hounsfield, Redhill, England).

The results are collected in the following tables:

TABLE I mechanical properties

|  | Knit A | | Knit B | | Knit C | |
| --- | --- | --- | --- | --- | --- | --- |
|  | Warp | Weft | Warp | Weft | Warp | Weft |
| Tensile breaking strength (N) | 175 ± 12 | 129 ± 2 | 187 ± 16 | 149 ± 10 | 237 ± 6 | 201 ± 6 |
| Elongation under 50 N (%) | 54 ± 0 | 50 ± 6 | 43 ± 1 | 59 ± 1 | 38 ± 1 | 46 ± 0 |
| Bursting strength (kPa) | 280 ± 19 | | 361 ± 38 | | 463 ± 19 | |
| Tear strength (N) | 22 ± 1 | 23 ± 2 | 23 ± 2 | 22 ± 3 | 30 ± 1 | 37 ± 5 |
| Suture pull out strength (N) | 32 ± 4 | 36 ± 1 | 33 ± 1 | 33 ± 2 | 46 ± 5 | 42 ± 3 |
| Tensile strength (N/cm) | 24 ± 1 | | 40 ± 1 | | 47 ± 1 | |

TABLE II mass per unit area and porosity

|  | Knit A | Knit B | Knit C |
| --- | --- | --- | --- |
| Mass per unit area (g/cm$^2$) | 45 | 36 | 46 |
| Thickness (mm) | 0.4 | 0.4 | 0.6 |
| Pore size (mm) (width × height) | 1.5 × 1.5 | 1.6 × 1.4 | 2.0 × 2.4 |
| Efficient porosity (%) | 53 | 35 | 55 |

With reference to Table I above, the knit of the invention (Knit C) shows improved mechanical properties in comparison with the knits of the prior art (Knits A and B). In particular, the knit of the invention shows a higher tensile breaking strength both in warp and weft directions than Knits A and B. The knit of the invention shows a higher bursting strength than Knits A and B. The knit of the invention shows a higher tear strength both in warp and weft directions than Knits A and B.

The knit of the invention (Knit C) shows an improved suture pull out strength both in warp and weft directions compared to the knits of the prior art (knits A and B). The knit of the invention shows a higher tensile strength both in warp and weft directions than Knits A and B.

With reference to Table II above, the knit of the invention further shows an improved efficient porosity compared to Knits A and B.

In addition, the system described at FIGS. 3 and 4 has been utilized to assess the following properties of knits A, B and C under various simulated physiological conditions. For proceeding to these measures, the textile-based implant 400 of FIGS. 3 and 4 is replaced by the knit sample, either Knit A, B or C, to be evaluated.

Figure 5:
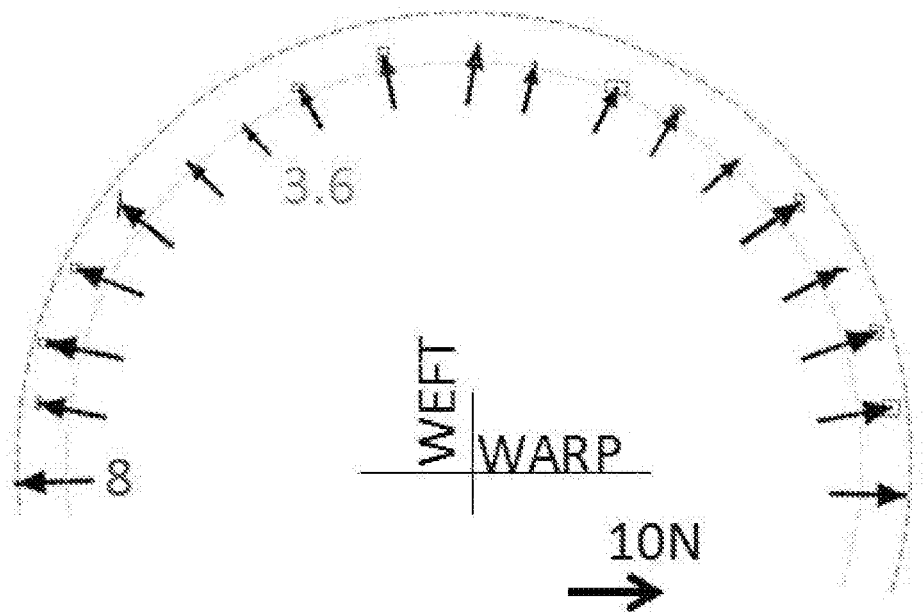
FIGS. 5 and 6 are schematic views of the form used to obtain the average distribution of shear forces at fixation points, as described in at least one embodiments herein.
Figure 6:
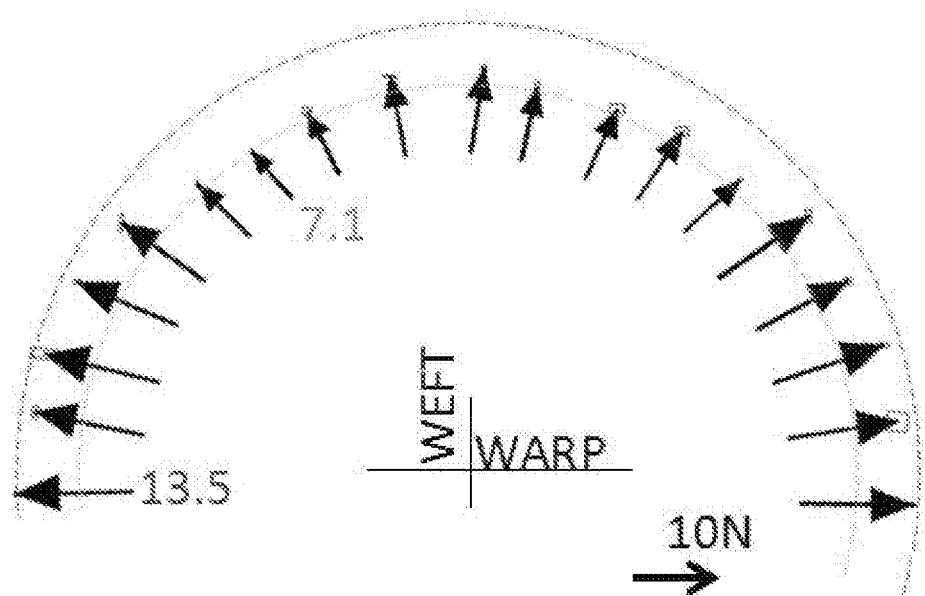

The following properties have been evaluated:

1°) The shear forces distribution profile at fixation points of the knit: for each plunger force, namely 147 N respectively 304 N, the marker displacement as described above is transformed into the shear force at each fixation point where markers exist from the initial fixation position, using the mechanical continuum theory applied to the rods implemented in the software MATLAB® from the company Matchworks. The shear force vector is recorded. The Max and min vector norm values are recorded. The average distribution of shear forces at fixation points may be obtained under the form as shown in each of FIGS. 5 and 6, with reference to the following plunger forces, respectively:

Plunger force: 147 N Plunger force: 304 N

Figure 7:
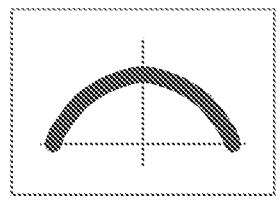
FIG. 7 is a schematized graph profile of the shear force distribution of a knit.

The shear forces distribution may be schematized by the graphic profile shown in FIG. 7.

An Average force Min-Max (N) is determined: on the example of the profile above, the Average force Min-Max (N) at a plunger force of 147 N is 3.8-8 and the Average force Min-Max (N) at a plunger force of 304 N is 7.1-13.5

For a knit, when the range of the value of the Average force Min-Max is low, the risks of failure of the knit are decreased. The knit and therefore the abdominal wall repair will be more efficient.

In addition, the more the profile of the shear forces is close to a semi-circle or a semi-ellipse, the more regularly the shear forces are distributed. The risks of tensions in a specific direction are therefore decreased. In addition, the forces being of similar values in all directions, the knit may be implanted without having to check for a specific position of the warp or weft direction of the knit. The knit, or the prosthesis made from the knit, will also be more comfortable for the patient.

2°) The bulging indication: corresponds to the distance in mm of penetration of the plunger 210 as described in FIGS. 3 and 4, from an initial position in which its contacting surface 212 is tangent to the sample knit to a final position obtained after application of the plunger force.

A too high bulging indication, like for example above 50 mm at a plunger force of 304 N or for example above 45 mm at a plunger force of 147 N, may mean that the knit/prosthesis may be two soft for ensuring its reinforcement function of the abdominal wall, and/or may generate discomfort and/or aesthetics disturbance.)

3°) The rupture of knit at fixation: the number of ruptures at fixation points is recorded.

Figure 8:
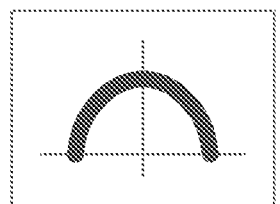
FIGS. 8-10 are schematized contour profiles of Knits A, B, and C, respectively.
Figure 9:
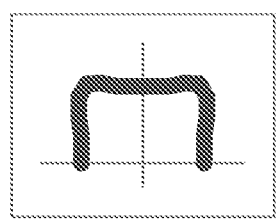
Figure 10:
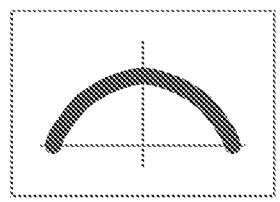

The results are collected in the following table:

The contour profile of Knits A, B, and C are shown in FIGS. 8-10, respectively.

TABLE III assessment of shear forces

| Knit | Average number of fracture at fixation points | Plunder force (N) | Average bulging indication (mm) | Average force Min-Max (N) |
|---|---|---|---|---|
| Knit A | 2 | 147 | 48 | 3.9-4.8 |
|  |  | 304 | 58.7 | 6.5-8.6 |
| Knit B | 2 | 147 | 44.6 | 2.2-5.7 |
|  |  | 304 | 54.5 | 4.5-11.2 |
| Knit C | 0 | 147 | 40.2 | 3.6-8 |
|  |  | 304 | 48.3 | 7.1-13.5 |

As appears from the table above, the knit of the invention (Knit C) shows a regular contour profile very close to a semi-circle. The shear forces are therefore regularly distributed. The knit of the invention may therefore be introduced at the implantation site and implanted without the surgeon having to check previously for a specific positioning of the warp or weft direction of the knit.

In addition, the number of fracture at fixation points is 0 for the knit of the invention, whereas it is 2 for the knits of the prior art (knits A and B). The knit of the invention is therefore more reliable once sutured or tacked to the surrounding biological tissues than the knits of the prior art.

Regarding the bulging indication, the knit of the invention (knit C) shows a better bulging indication at both plunger forces than the knits of the prior art. The knit of the invention will therefore ensure its reinforcement function of the abdominal wall and will be more efficient than the knits of the prior art in physiological conditions such as jumping or coughing.

The invention claimed is:

1. A prosthetic lightweight porous knit for hernia repair comprising a monofilament of a biocompatible polymer material having a diameter from about 0.08 mm to about 0.25 mm, wherein the knit comprises a mass per unit area ranging from about 40 to about 70 g/m$^2$, an efficient porosity ranging from about 30% to about 70%, and a suture pull out strength in a warp direction of at least 35 N and a suture pull out strength in a weft direction of at least 38 N.

2. The prosthetic lightweight porous knit of claim 1, wherein the knit comprises a pattern followed for knitting of the monofilament on knitting machine having two guide bars B1, B2 according to ISO 11676 standard, wherein the pattern of bar B1 is:

1.2/4.5/4.3/4.5/4.3/1.0/1.2/1.0//.

3. The prosthetic lightweight porous knit of claim 1, wherein the knit comprises a pattern followed for knitting of the monofilament on knitting machine having two guide bars B1, B2 according to ISO 11676 standard, wherein the pattern of bar B2 is:

4.3/1.0/1.2/1.0/1.2/4.5/4.3/4.5//.

4. The prosthetic lightweight porous knit of claim 1, wherein the biocompatible polymer material is selected from group consisting of polypropylene, polyethylene terephthalate, polyamide, silicone, polyether ether ketone (PEEK), polyarylether ether ketone (PAEK), polylactic acid (PLA), polycaprolactone (PCL), polydioxanone (PDO), trimethylene carbonate (TMC), polyvinyl alcohol (PVA), polyhydroxyalkanoate (PHA), polyglycolic acid (PGA), copolymers of these materials, and mixtures thereof.

5. The prosthetic lightweight porous knit of claim 1, wherein the biocompatible material is polypropylene.

6. The prosthetic lightweight porous knit of claim 1, wherein the diameter of the monofilament is from about 0.10 mm to about 0.15 mm.

7. The prosthetic lightweight porous knit of claim 1, wherein the diameter of the monofilament is about 0.12 mm.

8. The prosthetic lightweight porous knit of claim 1, wherein the knit comprises a plurality of pores having a diameter above 2 mm.

9. The prosthetic lightweight porous knit of claim 1, wherein the efficient porosity of the knit is about 55%.

10. The prosthetic lightweight porous knit of claim 1, wherein the mass per unit area of the knit ranges from about 44 g/m$^2$ to about 48 g/m$^2$.

11. The prosthetic lightweight porous knit of claim 1, wherein the knit comprises a tensile breaking strength in a warp direction of at least 200 N.

12. The prosthetic lightweight porous knit of claim 1, wherein the knit comprises a tensile breaking strength in a weft direction of at least 170 N.

13. The prosthetic lightweight porous knit of claim 1, wherein the knit comprises a bursting strength of at least 400 kPa.

14. The prosthetic lightweight porous knit of claim 1, wherein the knit comprises a tear strength in a warp direction of at least 25 N.

15. The prosthetic lightweight porous knit of claim 1, wherein the knit comprises a tear strength in a weft direction of at least 25 N.

16. A prosthetic lightweight porous knit comprising a monofilament of a biocompatible polymer material having a diameter from about 0.08 mm to about 0.25 mm, wherein the knit comprises a mass per unit area ranging from about 40 to about 70 g/m$^2$, a plurality of pores having a diameter above 2 mm, a tensile strength of at least 42 N/cm.

17. A method of hernia repair comprising
implanting a prosthetic lightweight porous knit in an extraperitoneal site of a patient, the prosthetic lightweight porous knit including a monofilament of a biocompatible polymer material, the knit comprising a pattern followed for knitting of the monofilament on a knitting machine having two guide bars B1, B2 according to ISO 11676 standard:
Bar B1: 1.2/4.5/4.3/4.5/4.3/1.0/1.2/1.0//
Bar B2: 4.3/1.0/1.2/1.0/1.2/4.5/4.3/4.5//, and
fixing the prosthetic light weight porous knit to surrounding tissues of the extraperitoneal site of the patient.

* * * * *